US00PP08139P

United States Patent [19]

Coward

[11] Patent Number: Plant 8,139

[45] Date of Patent: Feb. 9, 1993

[54] CHRYSANTHEMUM PLANT NAMED EARLY VERO

[75] Inventor: Matthew G. Coward, Punta Gorda, Fla.

[73] Assignee: Burdette Coward & Co., Inc., Punta Gorda, Fla.

[21] Appl. No.: 654,036

[22] Filed: Feb. 12, 1991

[51] Int. Cl.[5] ..... A01H 5/00

[52] U.S. Cl. ..... Plt./82.1

[58] Field of Search ..... Plt./74, 82.1

[56] References Cited

U.S. PATENT DOCUMENTS

P.P. 6,399 11/1988 Duffett et al. ..... Plt. 74

*Primary Examiner*—James R. Feyrer

*Attorney, Agent, or Firm*—Foley & Lardner

[57] ABSTRACT

A Chrysanthemum plant named Early Vero particularly characterized by its flat capitulum form; daisy capitulum type; white ray floret color; diameter across face of capitulum of up to 8 cm at maturity; flowering response of 8 to 8½ weeks under natural season flowering; medium plant height when grown as a single stem, and 15 to 20 cm peduncles on open, terminal sprays. Early Vero differs from the parent cultivar Vero by its substantially earlier flowering response and somewhat shorter plant height.

1 Drawing Sheet

The present invention comprises a new and distinct cultivar of Chrysanthemum, botanically known as *Dendranthema grandiflora*, and referred to by the cultivar name Early Vero.

The new cultivar is a sport or mutation of the cultivar Vero, disclosed in U.S. Plant Pat. No. 6,399. The new cultivar was discovered by the inventor on May 7, 1989, as a single plant growing among plants of the parent cultivar Vero in production beds of Burdette Coward & Co. Inc., Punta Gorda, Florida. The new cultivar was detected due to its substantially earlier flowering response.

At the time of discovery, the new sport was essentially in full bloom while the flowers of Vero were still in, and in fact never finished beyond, the bud stage. This was the first attempt to flower Vero at that time of the year where daylength is longer and temperatures are higher. It was later discovered that in early to mid-November, another marginal period due to varying daylength and temperature, Early Vero uniformly flowers whereas Vero tends to delay until daylight decreases to a certain point. Generally, Vero will not flower before November 15 when grown in Punta Gorda, Fla. under conditions noted below. Under the same growing conditions, Early Vero flowers as early as November 2-3 based on natural growing conditions with no photoperiodic control. Thus, in early to mid-November, Early Vero provides an excellent cultivar to supply the normal market for Vero. This is a very important commercial advantage. It was verified later that Early Vero blooms earlier than Vero by up to one week, depending on time of year and growing conditions.

In view of the potential importance of the earlier flowering characteristic, the sport was removed from the production beds and subsequently asexually propagated Jul. 11, 1989. Such propagation clearly established that the unique combination of characteristics as herein disclosed for Early Vero, including earlier flowering, are firmly fixed and are retained through successive generations of asexual reproduction. The complete stability of Early Vero has manifested itself in further generations of propagation up to the present time.

The primary difference between Early Vero and Vero is in the flowering response period. The only other differences noted to date are that Early Vero tends to be slightly shorter in overall height than Vero, and the flowering period of Early Vero extends from early to at least mid-May, and flowering also occurs in early November, as above described. The shorter plant height of Early Vero is probably due to the fact that it buds faster and has several days less to grow. The difference in height is usually not more than approximately 3". Besides flowering response and the extended flowering periods of Early Vero, the characteristics of Early Vero and Vero appear to be identical. This is of particular significance since Vero is now recognized as perhaps the most outstanding white daisy cut spray mum on the market today.

It should be noted that the earlier flowering response of Early Vero has always expressed itself, but varies depending on the time of the year. For example, based on natural growing conditions in Punta Gorda, Fla. during late November, plants of Early Vero bloom approximately 6-7 days before plants of Vero. As the season progresses and the day length decreases in December and January, the difference in response periods between the respective cultivars tends to decrease. In those months Early Vero blooms approximately 3-4 days ahead of Vero. As the days again become longer moving toward spring, the relative difference in flowering response time again increases. From mid-April to early May, under natural flowering at production facilities in Punta Gorda, Early Vero again blooms approximately 6-7 days ahead of Vero. An important distinction is that by mid-May, Vero, which is more sensitive to day length, slows down and actually stops flowering while Early Vero continues to bloom. The term "sensitive" is used to signify reaction of the plant to longer days in natural growing conditions. The earlier flowering response of Early Vero is of substantial economic advantage to growers. To those growers who are trying to maximize the natural season of Chrysanthemum production, it offers the option to extend the season both at the start and finish (early November and to and past mid-May). Thus, growers in Florida have the opportunity to reliably harvest Early Vero for Mother's Day and Thanksgiving. Vero will not flower dependably during those times, bearing in mind that shipments of cut flowers normally begin 10–14 days before each holiday.

For greenhouse growers the earlier flowering of Early Vero allows growers to recrop faster and accordingly make more efficient use of the areas devoted to pompon Chrysanthemum crops.

Early Vero has not been observed under all possible environmental conditions. The phenotype may vary significantly with variations in environment such as temperature, light intensity and daylength, without however, any variation in genotype. For example, trials to date have not included flowering of Early Vero beyond mid-May since it is normal to maximize production for the Mother's Day holiday, and the quality of flowers significantly deteriorates at that time due to daylength and possibly temperature. It has been determined that Early Vero will flower uniformly in Florida until at least mid-May, and it may very well flower well beyond that day under natural light conditions.

The following observations, measurements and comparisons describe plants of Early Vero grown in Punta Gorda, Fla. under natural season conditions which approximate those generally used in commercial practice. Natural season in Punta Gorda is between approximately November 1 through at least mid-May, and black cloth covering is not used. The plants are grown under saran cloth with 30% shade and no heat. During periods of decreased light in winter, lights are used to produce long days prior to the start of short days.

Tests have not been conducted on Early Vero under strict photoperiodic control regimens consisting of precise black cloth application. However, under short daylength natural growing conditions in mid-winter in Punta Gorda, it is expected that the difference between Vero and Early Vero in flowering response periods under a primarily photoperiodic regimen will be between 4–7 days.

The following traits have been repeatedly observed and are determined to be basic characteristics of Early Vero, which, in combination, distinguish this Chrysanthemum as a new and distinct cultivar:

1. Flat capitulum form.
2. Daisy capitulum type.
3. White ray floret color.
4. Diameter across face of capitulum up to 8 cm at maturity.
5. The natural season flowering response ranges from 8–9 weeks, depending on the time of the year. For example, as above noted, short day treatment beginning September 1 will produce flowering November 2–3. In mid-winter, the flowering response is a uniform 8 weeks.
6. Peduncle length ranges from 15 to 20 cm on open terminal sprays.
7. Medium plant height, requiring two long day weeks prior to short days to attain a flowered plant height of 100 to 110 cm for year-round flowerings. Early Vero is approximately 2–3 inches shorter than Vero when grown in Punta Gorda, Florida.
8. Its ability to uniformly flower in early to at least mid-May, and in early to mid-November.

The accompanying black and white photographic drawing shows the earlier flowering response of Early Vero when compared to Vero. The bunch of flowering stems appearing on the left comprise Early Vero essentially in full bloom, with the bunch on the right comprising stems of Vero in the bud stage. The plants from which the stems were cut were stuck September 25, planted in the field October 9, pinched October 24, subjected to short day treatment beginning November 25, and harvested January 21.

Of the commercial cultivars shown to the inventor, the most similar in comparison to Early Vero is Vero. As above noted, Early Vero is identical to Vero except for its earlier flowering, somewhat shorter height, and the ability to bloom during the longer daylength periods of May and November.

Early Vero can also be compared to the well known commercial white daisy White Marble. The response of White Marble is generally the same as Vero, although White Marble will bloom, although non-uniformly, until mid-May and a few days earlier in November. Early Vero extends this daylength period of flowering, as noted. In early May flowerings, White Marble tends to exhibit foliage deterioration, increased bracting in the disc, and downward reflexing of the petals. In addition, Early Vero, similar to Vero, is distinguished from White Marble by its more pure white flower color, superior foliage, and somewhat smaller flower diameter.

In the following description color references are made to The Royal Horticultural Society Colour Chart. The pure white ray floret color of Early Vero is not exactly represented in The Royal Horticultural Society Colour Chart.

Classification:

*Botanical.*—*Dendranthema grandiflora* cv Early Vero.

*Commercial.*—Daisy cut spray mum.

INFLORESCENCE

A. Capitulum:

*Form.*—Flat.

*Type.*—Daisy.

*Diameter across face.*—Up to 8 cm at maturity.

B. Corolla of ray florets:

*Color (general tonality from a distance of three meters).*—White.

*Color (upper surface).*—White.

*Color (under surface).*—White.

*Shape.*—Flat, oblong.

C. Corolla of disc florets:

*Color (mature).*—14A to 14B.

*Color (immature).*—145A.

D. Reproductive organs.

*Androecium.*—Present on disc florets only; scant pollen.

*Gynoecium.*—Present on both ray and disc florets.

PLANT

A. General appearance:

*Height.*—Medium; 100 to 110 cm as a flowering plant from a rooted cutting.

B. Foliage:

*Color (upper surface).*—147A.

*Color (under surface).*—147B.

*Shape.*—Lobed, slightly serrated.

I claim:

1. A new and distinct Chrysanthemum plant named Early Vero, as described and illustrated.

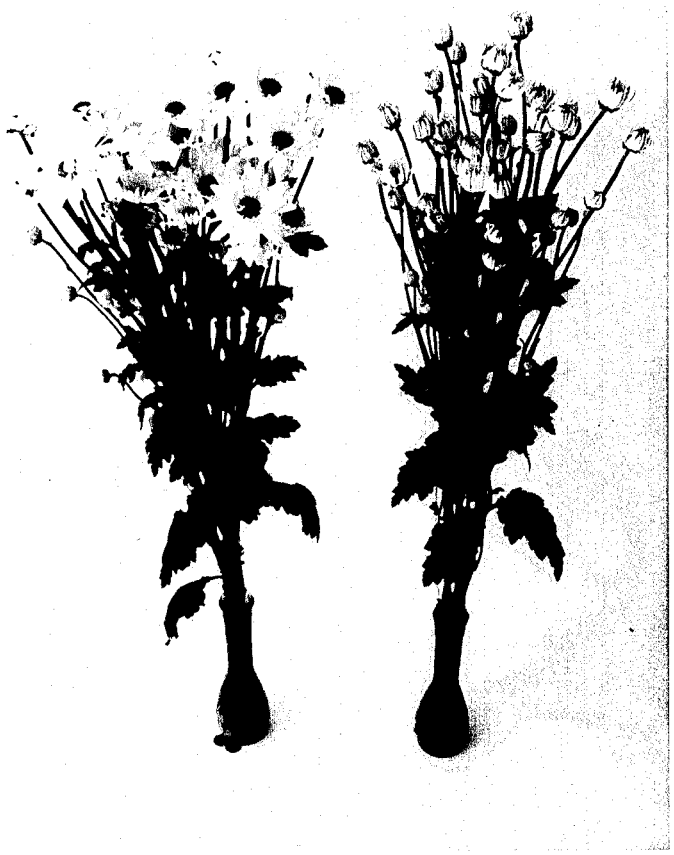

* * * * *